US 6,663,593 B2

(12) United States Patent
Ito

(10) Patent No.: US 6,663,593 B2
(45) Date of Patent: Dec. 16, 2003

(54) DISPOSABLE SYRINGE WITH PLUNGER RUPTURE

(76) Inventor: Roberto Yassuo Ito, c/o Edmundo Brunner Assessoria Av. Brigadeiro Louis Antonio, 4329, Sao Paulo (BR), CEP 01401-002

( * ) Notice: Subject to any disclaimer, the term of this patent is extended or adjusted under 35 U.S.C. 154(b) by 67 days.

(21) Appl. No.: 10/015,306

(22) Filed: Dec. 12, 2001

(65) Prior Publication Data
US 2003/0109831 A1 Jun. 12, 2003

(30) Foreign Application Priority Data
Jul. 25, 2001 (BR) .......................... 8101570 U

(51) Int. Cl.$^7$ .......................... A61M 5/00; A61M 5/315
(52) U.S. Cl. ........................ 604/110; 604/228
(58) Field of Search .......................... 604/110, 218, 604/228, 229, 187; 128/919

(56) References Cited
U.S. PATENT DOCUMENTS

| 4,144,885 | A | * | 3/1979 | Stait | 128/218 P |
| 4,973,308 | A | * | 11/1990 | Borras et al. | 604/110 |
| 4,973,309 | A | | 11/1990 | Sultan | 604/110 |
| 5,181,912 | A | * | 1/1993 | Hammett | 604/110 |
| 5,215,524 | A | * | 6/1993 | Vallelunga et al. | 604/110 |
| 5,226,882 | A | * | 7/1993 | Bates | 604/110 |
| 5,352,203 | A | * | 10/1994 | Vallelunga et al. | 604/110 |
| 5,478,314 | A | * | 12/1995 | Malenchek | 604/110 |
| 5,643,211 | A | * | 7/1997 | Sadowski et al. | 604/110 |
| 5,722,951 | A | * | 3/1998 | Marano | 604/110 |
| 5,738,655 | A | | 4/1998 | Vallelunga et al. | 604/110 |
| 5,928,202 | A | * | 7/1999 | Linnebjerg | 604/228 |
| 6,409,704 | B1 | * | 6/2002 | Tsai | 604/110 |
| 2002/0035350 | A1 | * | 3/2002 | Turnbull et al. | 604/110 |

* cited by examiner

Primary Examiner—Sharon Kennedy
(74) Attorney, Agent, or Firm—Ware, Fressola, Van Der Sluys & Adolphson LLC; Milton Oliver

(57) ABSTRACT

A disposable syringe has a plunger rupture device and a washer-guide sealing barrel nozzle which make it safe against re-use, since the plunger breaks up and the piston is stuck at the bottom of the barrel, thereby making impossible reloading of the syringe. The syringe is assembled by fitting the pressure washer onto the plunger, fitting the rubber to the piston base, fitting the plunger to the piston, inserting the support bolt to the fitting of the set plunger/piston, fitting the assembled set plunger/piston into the barrel, and, finally, seating the screening washer inside the top of the barrel, thereby sealing the syringe entirely.

19 Claims, 13 Drawing Sheets

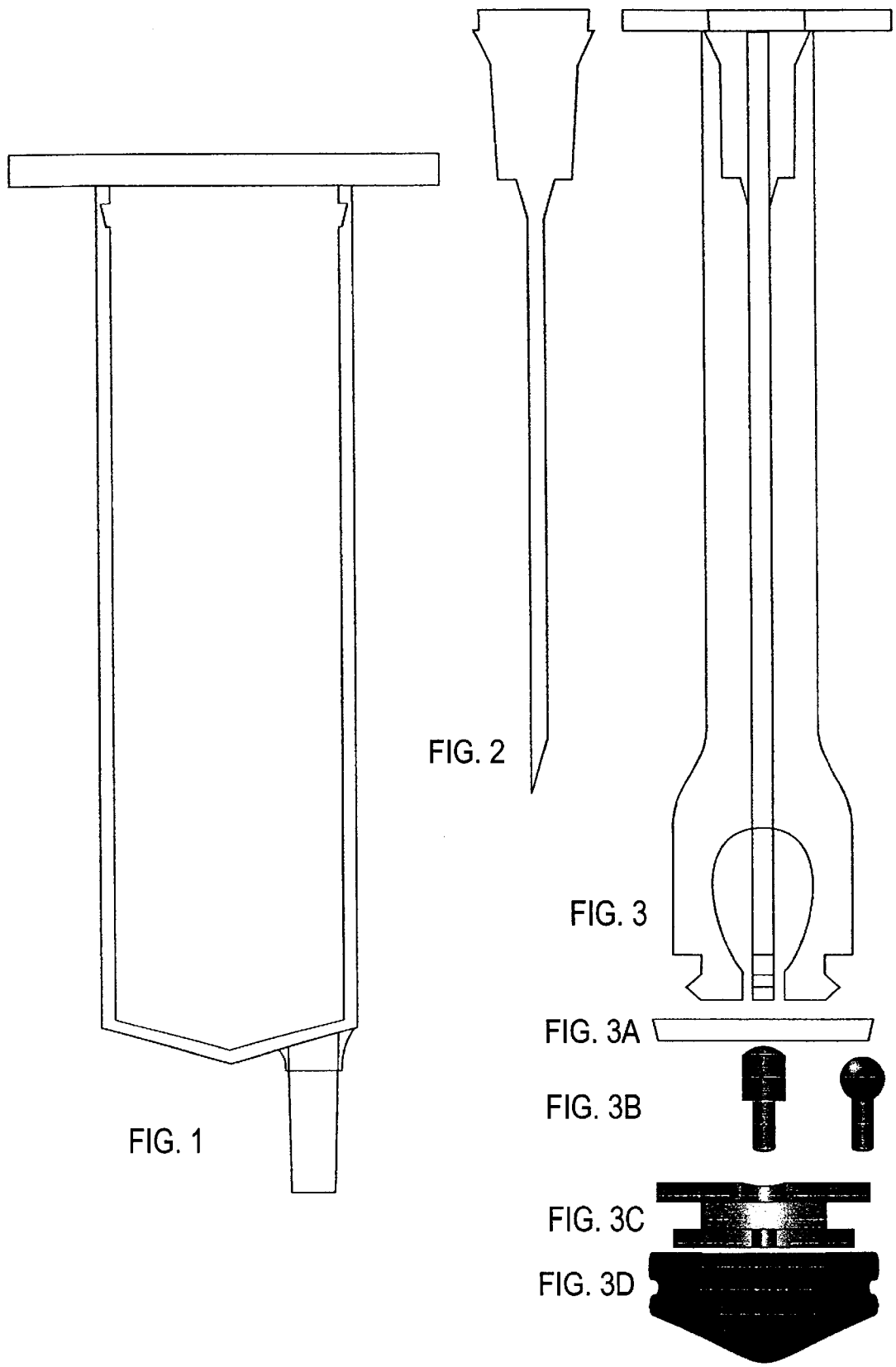

FIG. 6
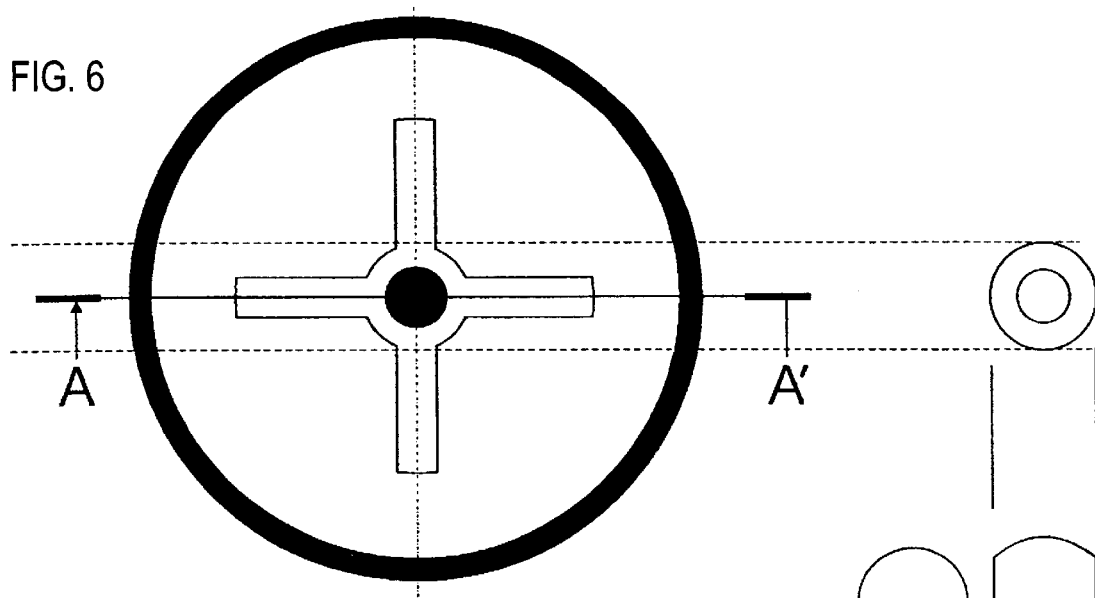
FIG. 6A  CUT A A'
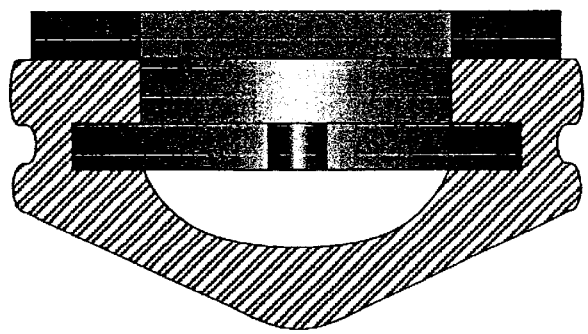
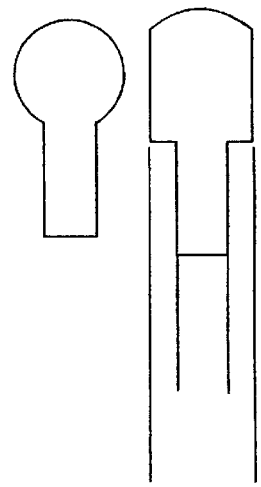
FIG. 7
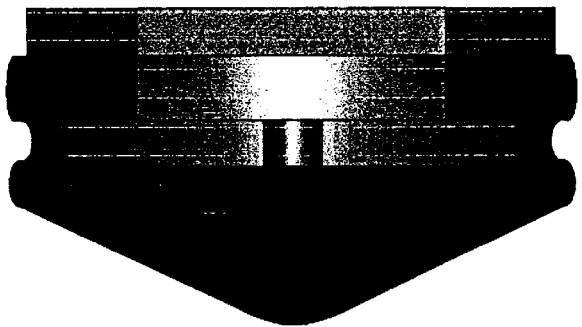
FIG. 8
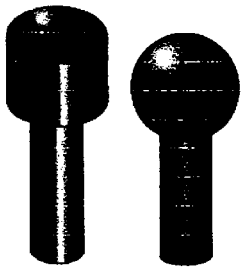

CUT A A'

CUT A A'

CUT A A'

LIQUID

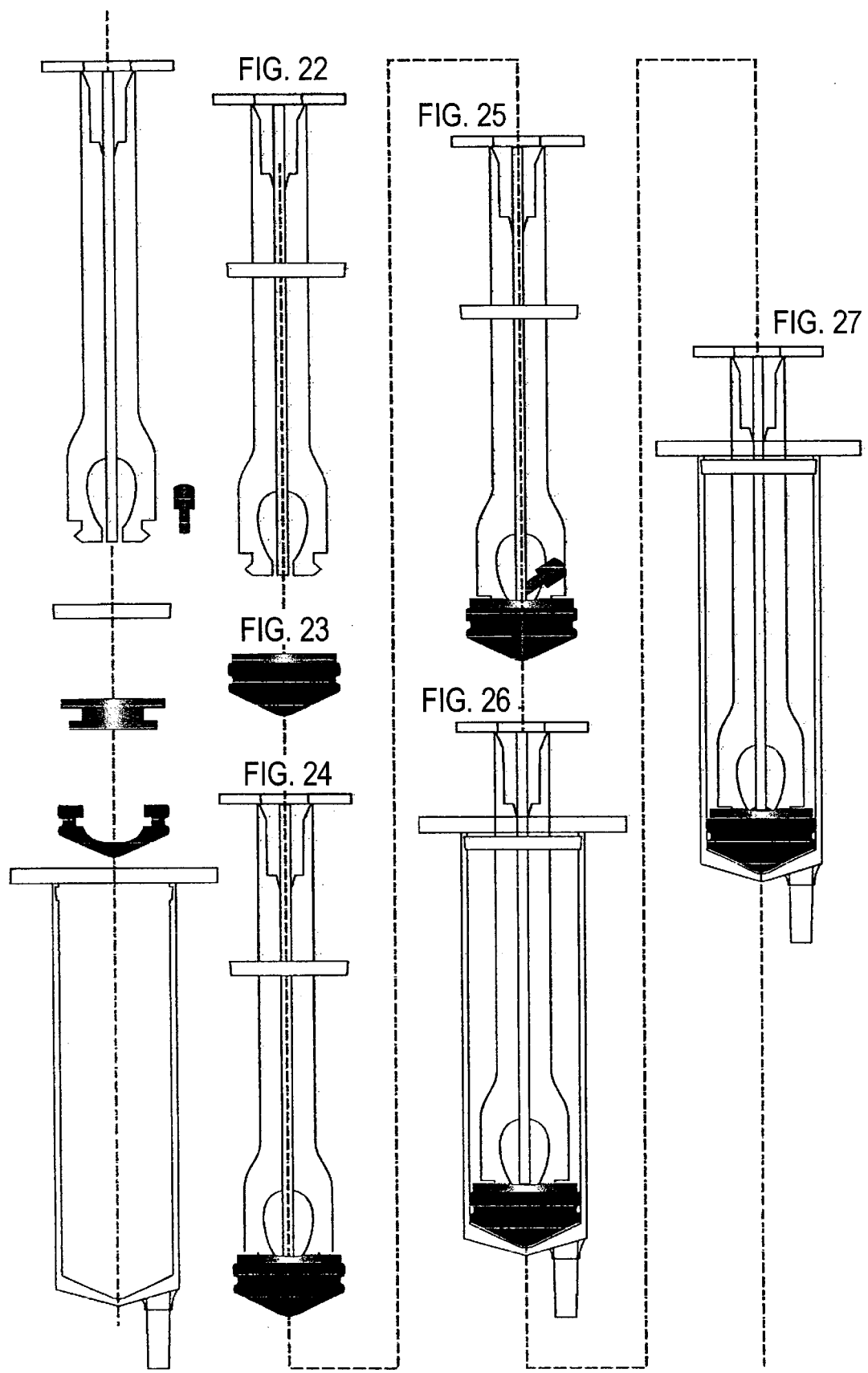

FIG. 28　　　FIG. 29　　　FIG. 29A　　　FIG. 29B
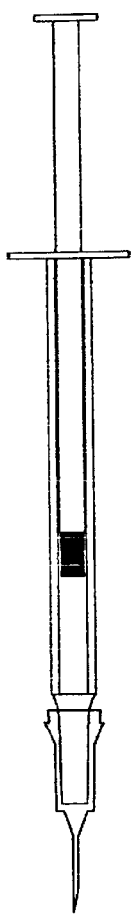
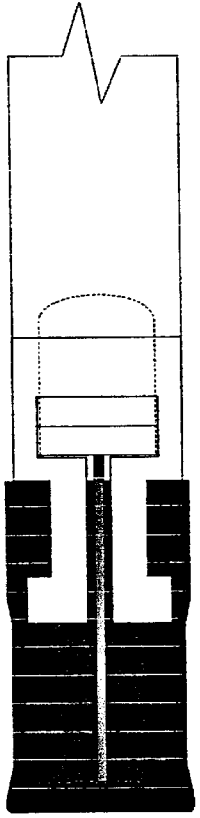
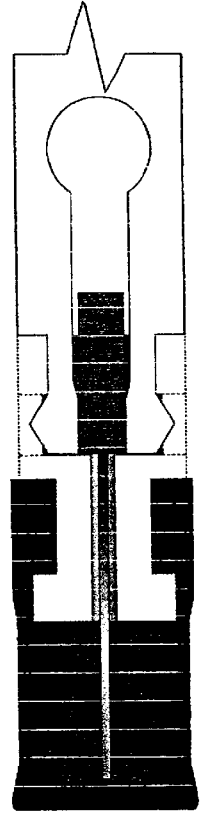
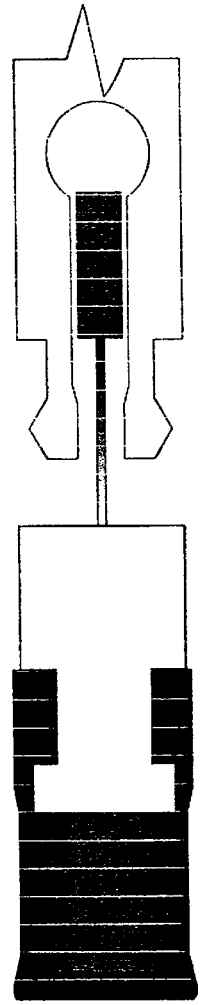
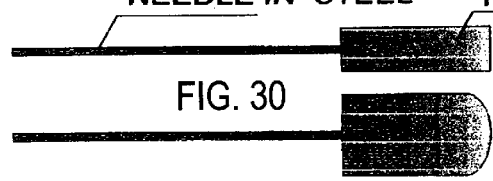
NEEDLE IN STEEL　　EXTREMITY IN PLASTIC
FIG. 30
PISTON RUBBER BASE
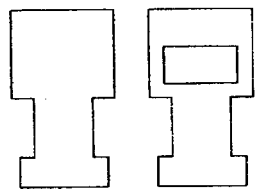
SCREENING WASHER-GUIDE
FIG. 31
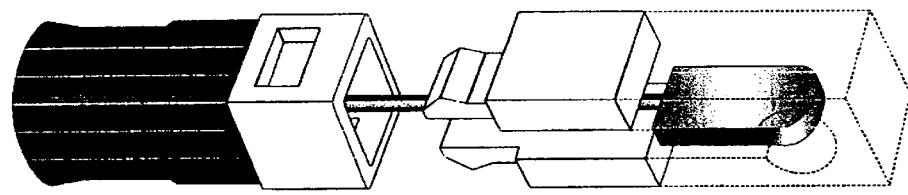

DISPOSABLE SYRINGE WITH PLUNGER RUPTURE

FIELD OF THE INVENTION

Disposable syringes: syringes that were supposed to be discarded after their use. Unfortunately, those syringes are being re-used, as proven by the statistics. About 25% of AIDS cases are directly attributable to disposable syringes.

BACKGROUND

There are several brands and models of syringes available in the market. However, no model is really disposable. They are only designed with the objective of guaranteeing the quality and sterility of the product. Therefore, it is of extreme importance that measures be taken so that these syringes can really be discarded, avoiding the burden of additional expenses to the health system due to their re-use. The warnings "To be used only once" or "To be destroyed after use!" printed in the packing don't guarantee that the product will be discarded. There are no secure ways of supervising the final user of the product. If each sold unit were really destroyed after its use, the cost with syringes would be ridiculous, when compared with the economy generated by the reduction of the health expenses attributable to the sharing of disposable syringes.

SUMMARY OF THE INVENTION

The present invention is about a "Disposable Syringe with a plunger rupture device" or, more accurately, about a device of automatic action which permits the syringe to be used only once. The syringe is characterized by a device that allows the charging of fluids as in any common syringe; however, when the piston has its course reversed, the pressure that the user exercises in the plunger, and, consequently, in the piston, receives a contrary pressure from the fluid. At this point, the device is triggered: the rubber suffers a deformation, expelling the support bolt from the set plunger/piston. This make the claws at the plunger lose their grip and the piston detaches itself from the plunger, getting stuck at the bottom of the barrel, making impossible a second use of the syringe.

BRIEF FIGURE DESCRIPTION

FIG. 1 is a sectional view of a syringe;

FIG. 2 schematically illustrates a needle;

FIG. 3 schematically illustrates a piston stem of the present invention;

FIG. 3A shows a guide washer used in the present invention;

FIG. 3B is a side view of a supporting pin or bolt 6;

FIG. 3C is a sectional view of a plunger body 22;

FIG. 3D shows a flexible elastomeric membrane 10 used to cover or surround a lower part of the plunger body 22;

FIGS. 6 & 6A are top and side views of the Plunger body;

FIG. 7 is a sectional view of the membrane 10;

FIG. 8 is a perspective view of the supporting pin or bolt;

FIGS. 15, 15A & 15B are, respectively, side, top, and perspective views of guide washer 21;

FIGS. 22–27 illustrate syringe components in different configurations; and

FIGS. 28–31 illustrate components of the syringe, enlarged.

DETAILED DESCRIPTION

The objective of this invention is to force the use of the syringe only a single time. The breaking of the device is the warranty against a possible re-use. In order to facilitate understanding of our invention, we are enclosing a detailed description of the device. We have used a 20 ml disposable syringe as an example.

Sheet 1/13—Components. Scale 1:2. Barrel (FIG. 1); Needle (FIG. 2); Plunger (FIG. 3); Piston rubber base (FIG. 3C); Rubber (FIG. 3D).

Sheet 2/13—Perspective view of the system. (FIGS. 8–13);

Sheet 3/13—Upper view of the piston rubber base (FIGS. 6–8). Scale 1:4;

Sectional view of the set rubber and base (FIG. 6A) Piston in its normal shape (FIG. 7) Scale 1:4. Support bolt (FIG. 8) scale 1:4.

Figure 4:
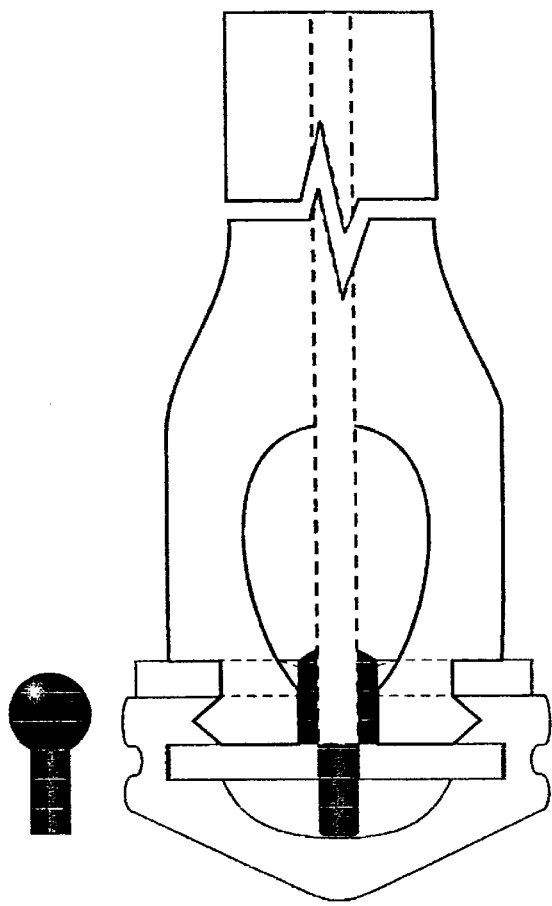
FIGS. 4 & 4A are sectional views showing how claws 5, 27 of the plunger engage and then disengage.
Figure 4A:
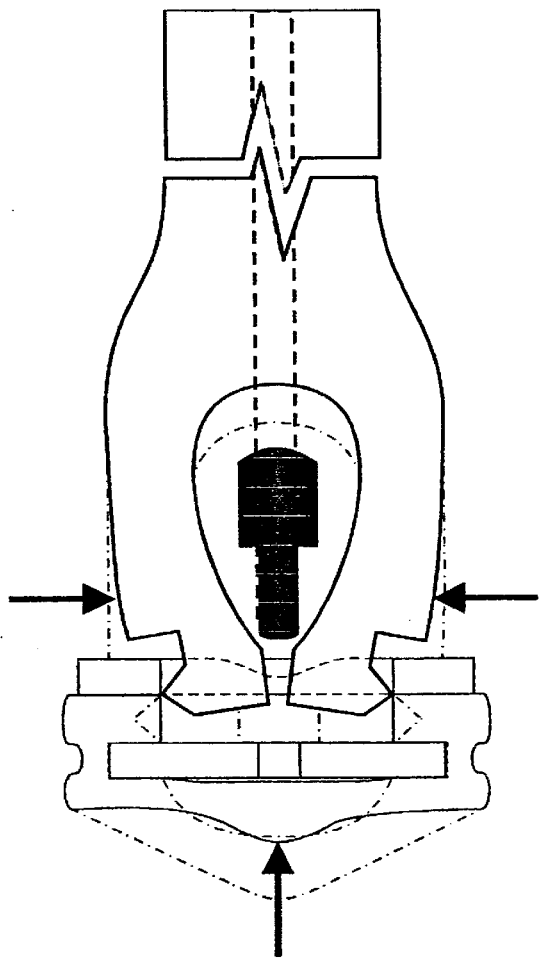
Figure 5:
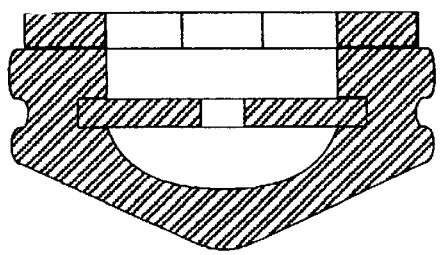
FIGS. 5 & 5A illustrate how flexible membrane 10 deforms.
Figure 5A:
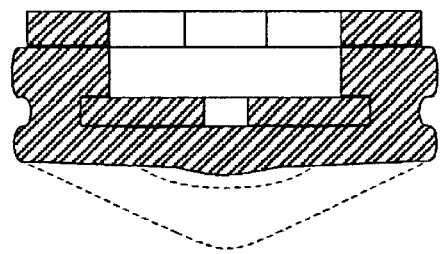
Figure 10:
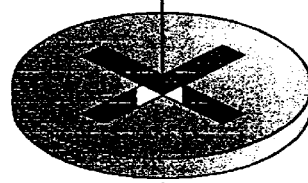
Figure 11:
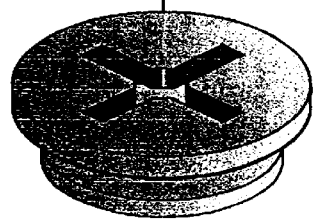
Figure 12:
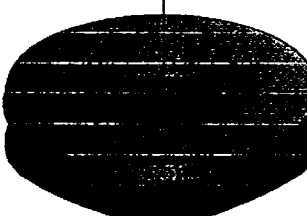
Figure 13:
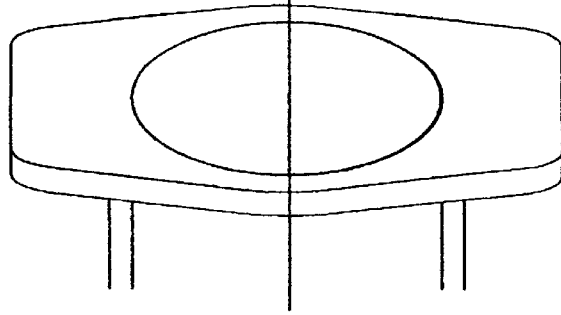
Figure 14:
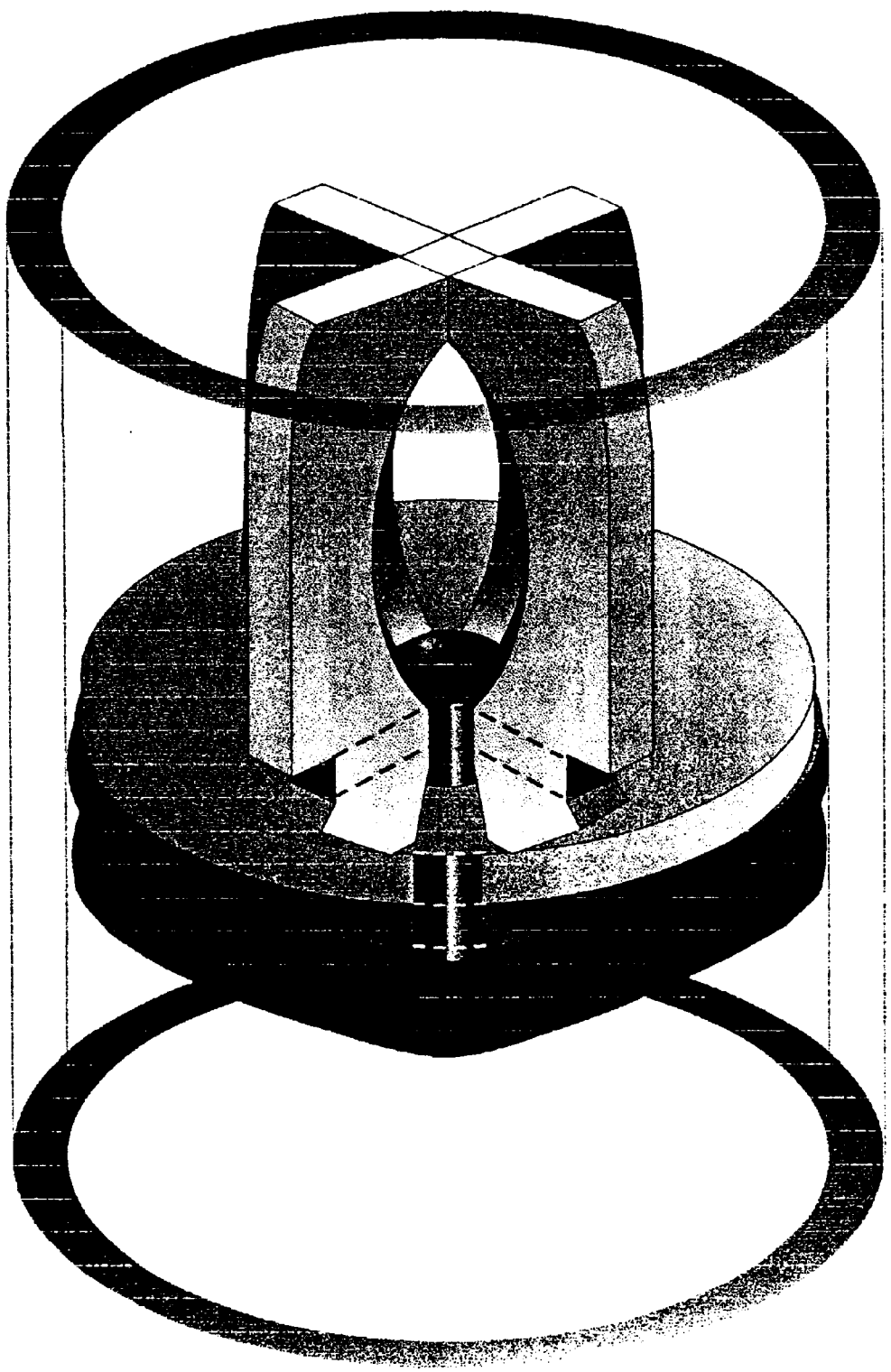
FIG. 14 is a perspective view showing components assembled.
Figure 15:
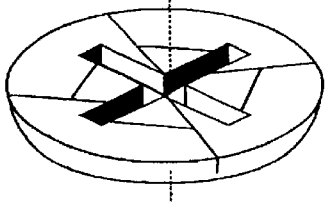
Figure 17:
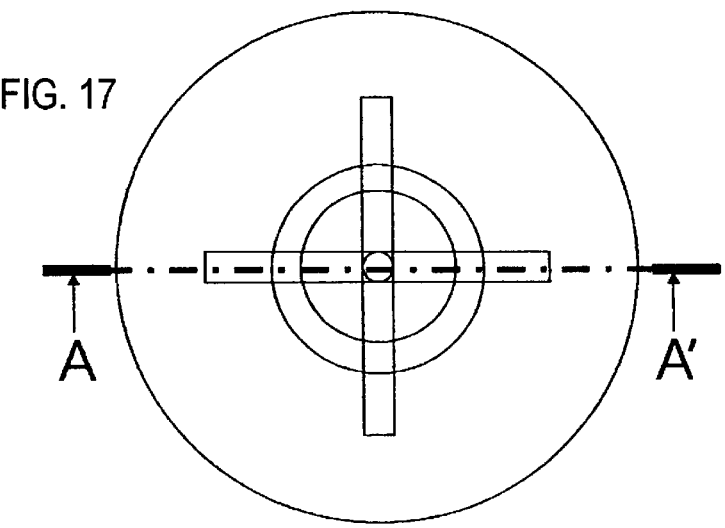
FIGS. 17 & 17A are top and side sectional views, illustrating insertion of a used needle into a central recess in the syringe.
Figure 17A:
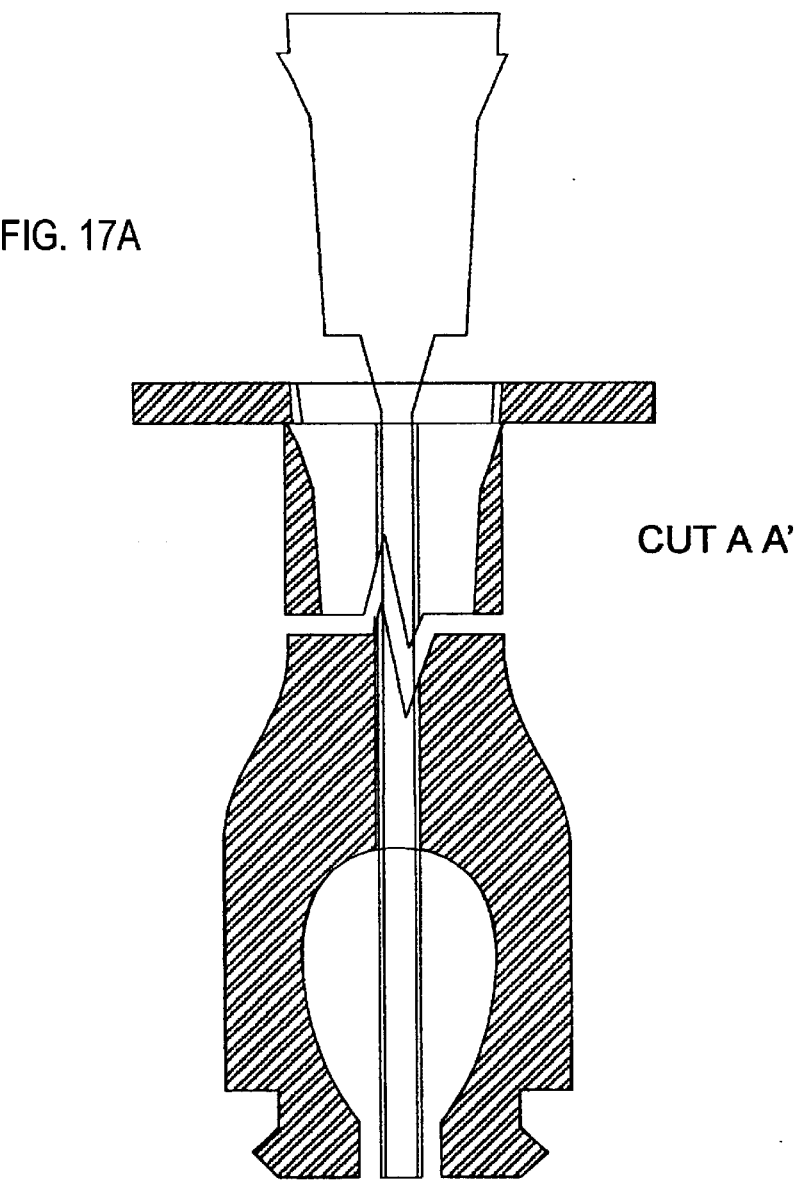

Sheet 4/13—Perspective view of the assembled device (FIG. 14);

Sheet 5/13—Top view of the plunger (FIG. 17) scale 1:3; A sectional view of the plunger (FIG. 17A). scale 1:3;

Sheet 6/13—Side view of the plunger claw (FIG. 4). scale 1:3;

A clearer illustration of the action of the claw (FIG. 4A). scale 1:3;

Rubber action of the piston (FIG. 5 and FIG. 5A). scale 1:3;

Sheet 7/13—Side sectional view of the sealing washer-guide (FIG. 15). scale 1:2.

Figure 15A:
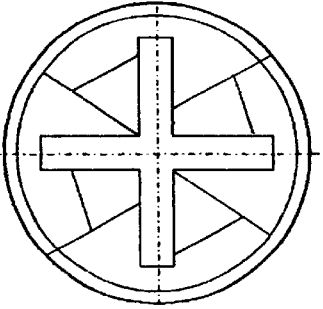

Top view of the washer sealing washer-guide (FIG. 15A), scale 1:2.

Washer-guide in perspective (FIG. 15B), scale 1:2.

Figure 16:
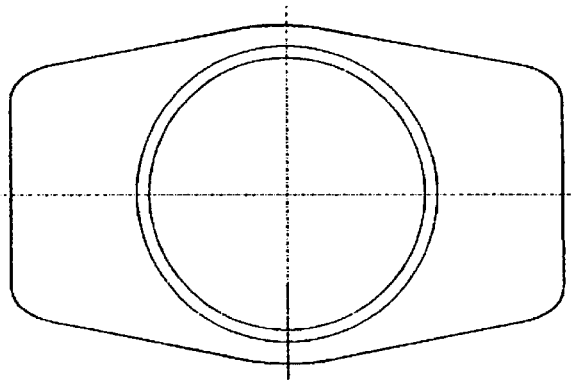
FIG. 16 is an end view of the syringe of the invention.

Top view of the nozzle of the barrel (FIG. 16), scale 1:2.

Figure 16A:
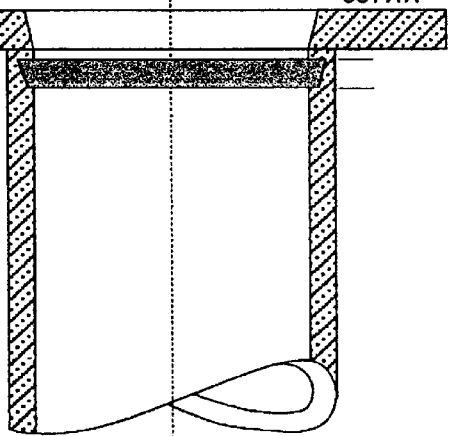
FIG. 16A is a sectional view of the end of the syringe.
Figure 16:
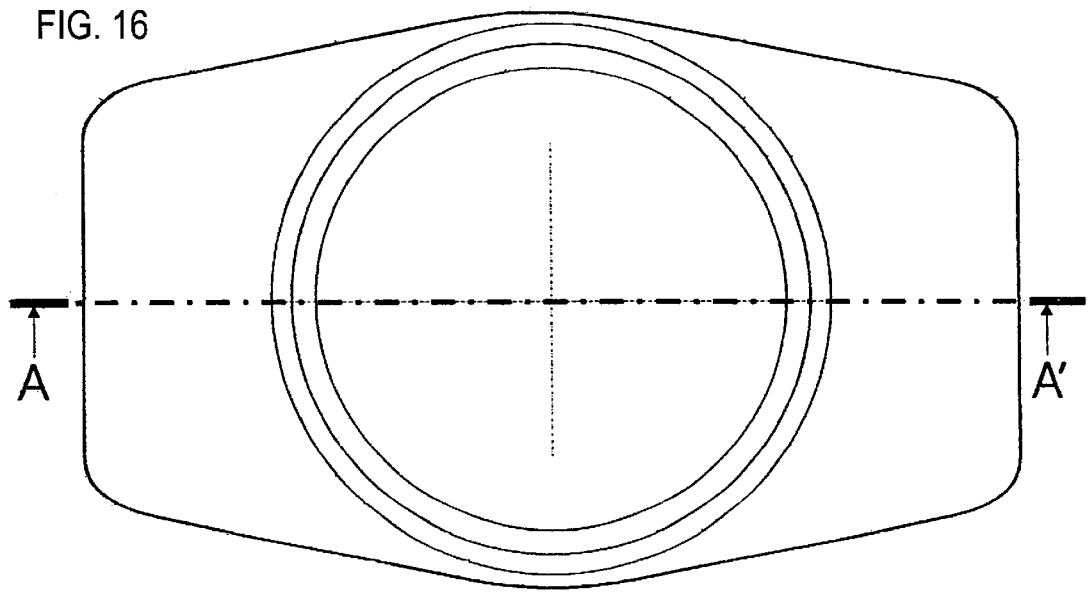
Figure 16A:
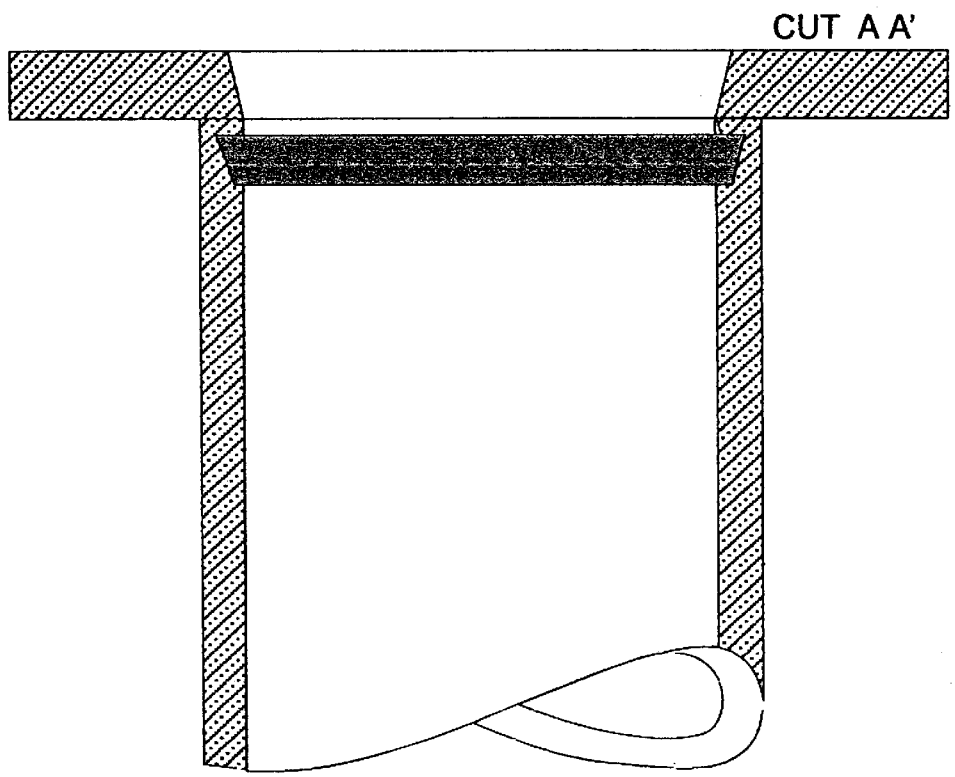

A sectional view of the barrel nozzle (FIG. 16A), scale 1:2.

Figure 9:
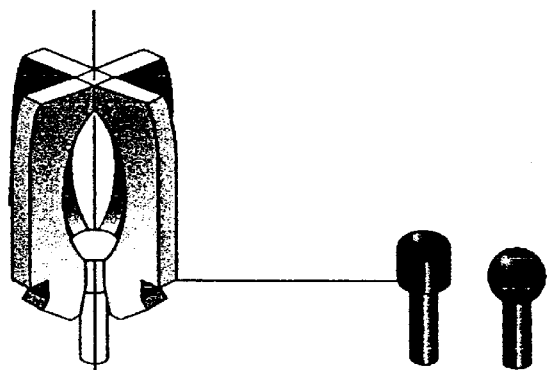
FIGS. 9–13 are perspective views of components of the present invention, aligned along a common central axis.
Figure 9A:
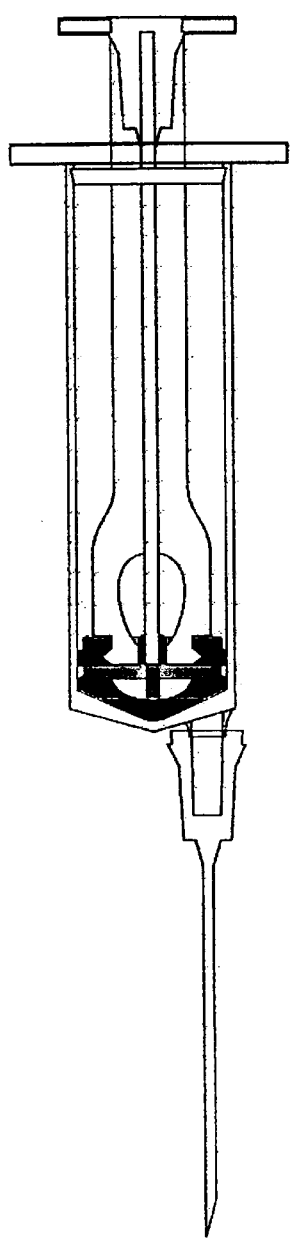
Figure 9B:
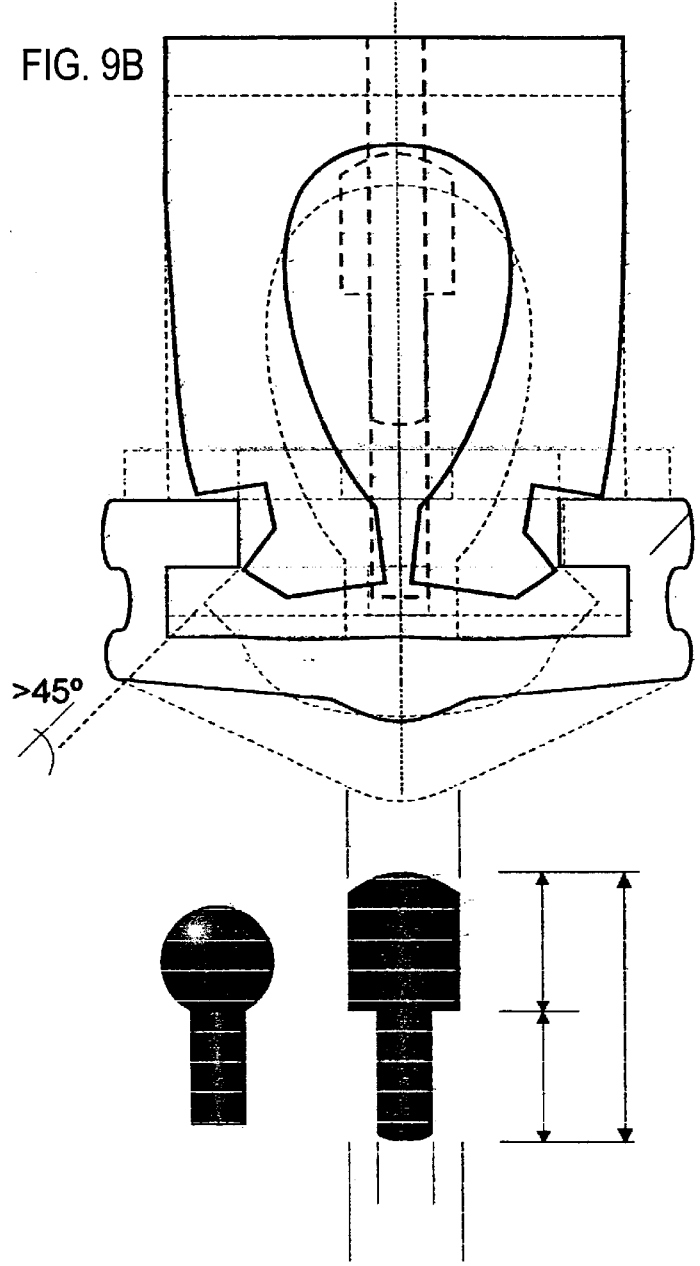
Figure 9C:
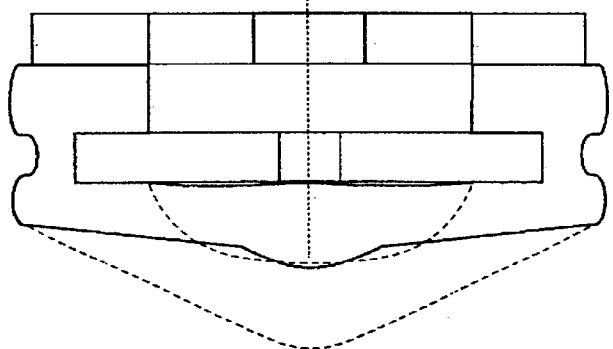

Sheet 8/13—Upper view of the barrel nozzle (FIG. 8). scale 1:4;

Sectional view of the barrel (FIG. 16A). scale 1:4;

Sheet 9/13—Syringe in its normal shape (FIG. 9A), scale 1:2; action of the claw after expelling the support bolt and retention of the plunger claws (FIG. 9B), scale 1:4. Action of the piston rubber (FIG. 9C) scale 1:4.

Figure 18:
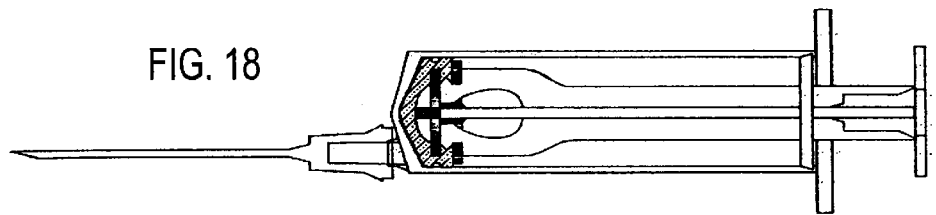
FIGS. 18 through 18D illustrate stages in the use of the syringe.
Figure 18A:
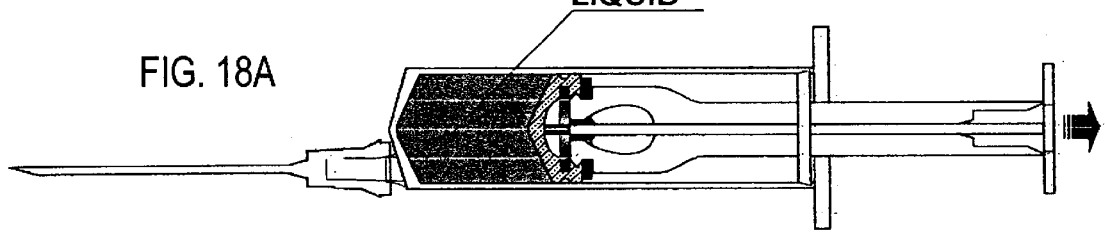
Figure 18B:
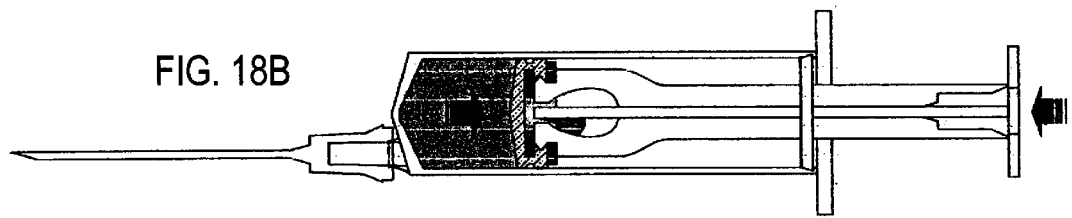
Figure 18C:
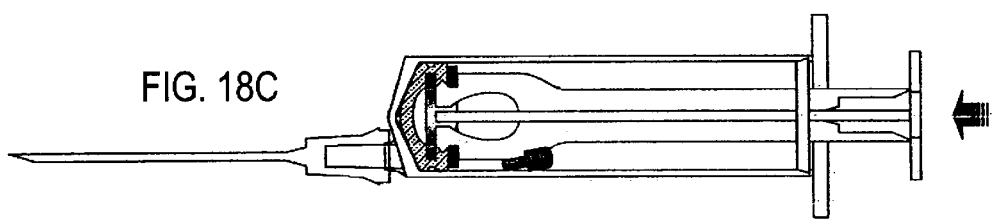
Figure 18D:
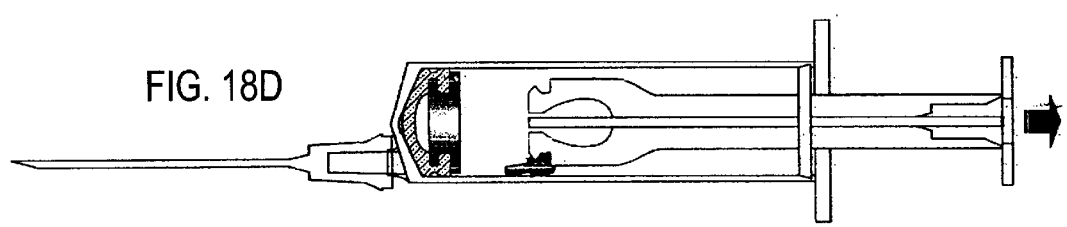
Figure 19:
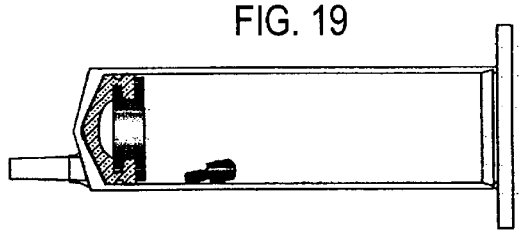
FIGS. 19 & 19A illustrate the syringe state after use.
Figure 19A:
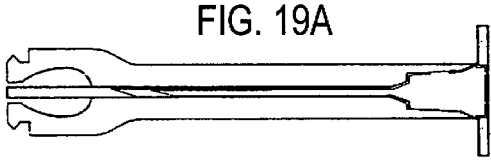
Figure 20:
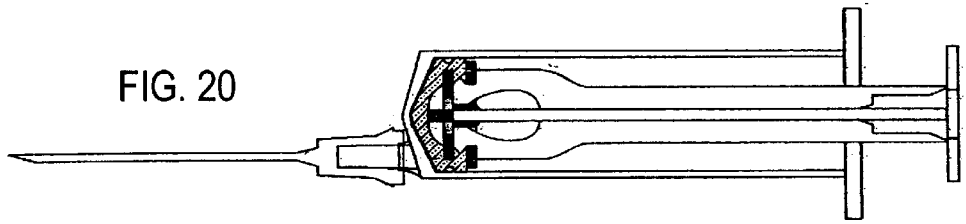
FIGS. 20–21B illustrate the syringe in case of attempted re-use without the washer-guide.

Sheet 10/13 (no scale). The assembled syringe as the final consumer will purchase in the market (ready for use) (FIG. 18). The process will be identical to that of common syringes, up to the point of charging of fluids (FIG. 18A). When the pressure is reversed, i.e., when the user presses the plunger to expel the fluid, the energy will be transferred proportionally to the piston, resulting in the deformation of the rubber. This deformity will automatically expel the "support bolt" from the plunger/piston set (FIG. 18B). Once the support bolt is expelled, the plunger loses its grip and it is disconnected from the piston, disabling the syringe (FIG. 18C). The plunger can then be removed from the barrel totally. However, the piston will be kept at the bottom of the barrel due to the release of the rubber (FIG. 18D & 19). The plunger itself will become a container for the used needle (FIG. 19A).

Figure 21:
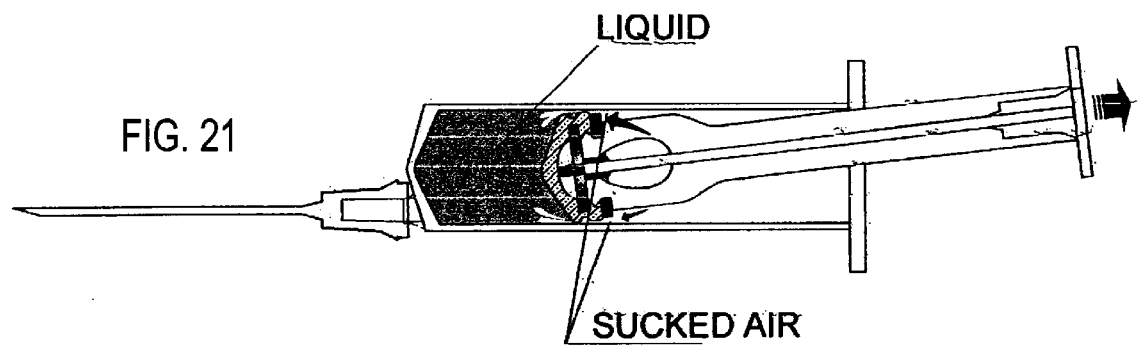
Figure 21A:
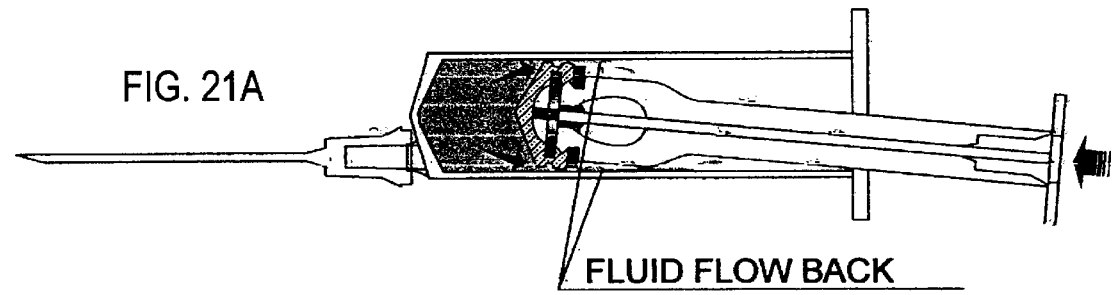
Figure 21B:
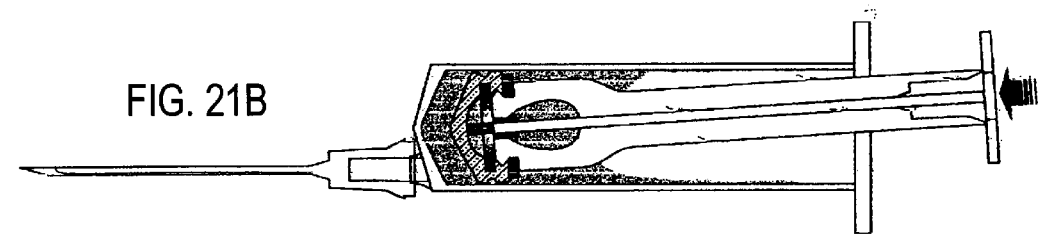

Sheet 11/13—(No scales)-Demonstration of the impossibility of a second use without the sealing washer-guide. Once without the washer-guide, the plunger loses its central alignment; consequently, the piston loses its perpendicularity and oscillates in relation to the wall of the barrel. In the charging process, the vacuum will suck in air (FIG. 21) and, in the injection, the pressure of the fluid being larger than the atmospheric pressure makes the fluid flow back (FIG. 21A), resulting in the loss of the fluid to be injected (FIG. 21B).

Sheet 12/13—Sequence for assembling the syringe. (FIGS. 22–27).

Sheet 13/13—Device for insulin syringes. (FIGS. 28–31).

What is claimed is:

1. A non-reusable syringe, comprising
    a generally cylindrical hollow barrel adapted for mounting an injection needle thereon at a proximal end thereof;
    a plunger adapted for longitudinal displacement within said barrel, formed at its proximal end with a plurality of radially flexible claws which, in an unflexed configuration, are spaced from each other by a space of predefined radius;
    an elastomeric piston having an outer rim adapted to engage against an inner surface of said barrel, said piston being formed on a distal surface thereof with a central recess including an annular internal groove adapted, during a normal configuration of said piston, to receive and engage said claws; and
    a bolt having a head portion and a shank portion, said shank portion being dimensioned to fill said space of predefined radius between said claws, and said head portion being dimensioned radially larger, to keep said bolt seated between said claws during a first fluid-charging stroke of said syringe,
    whereby, during a fluid-injecting stroke of said plunger, fluid pressure expels said bolt from between said claws and said elastomeric piston deforms, causing said claws to flex radially inward and to lose engagement with said annular groove, said plunger thereby detaching from said piston and rendering a second charging stroke of said syringe impossible.

2. A non-reusable syringe, according to claim 1, wherein said flexible claws are formed, at lower ends thereof, with bevels at an angle greater than 45°.

3. A non-reusable syringe, according to claim 1, further comprising an elongated piston stem (3) formed with a compartment (2) at the center of its outer end, said compartment (2) being adapted to accommodate a needle therein.

4. A non-reusable syringe, according to claim 3, further comprising
    a guide washer (21) formed with a central cutout (12), in the shape of a cross, for guiding the elongated piston stem (3).

5. A non-reusable syringe, according to claim 4, wherein the body of the guide washer (21) is formed with at least one groove (13), thereby rendering said washer frangible.

6. A non-reusable syringe, according to claim 5, wherein the guide washer (21) is welded at a groove (1) of the syringe body, by laser welding (14).

7. A non-reusable syringe, according to claim 1, further comprising an elongated body, named the stem, which has its length reduced longitudinally, to an extent sufficient to create oscillations, in case of any attempted reutilization of the syringe without the guide washer (21).

8. A non-reusable syringe, according to claim 1, further comprising an elongated body, named the stem, which is a separate element from a body (22) of said plunger.

9. A non-reusable syringe, according to claim 1, wherein said head portion of said bolt (6) has a generally cylindrical shape.

10. A non-reusable syringe, according to claim 1, wherein said head portion of said bolt (6) has a generally spherical shape.

11. A non-reusable syringe, according to claim 1, wherein a lower part (22) of said plunger includes a flexible elastomeric membrane whose thickness is reduced to create more flexibility.

12. A non-reusable syringe with a piston stem detachment system, comprising:
    a syringe body;
    a piston stem/plunger assembly, adapted to expel the liquid intended to be injected from the inside of the syringe, said piston stem/plunger assembly comprising a stem having an elongated body (3) that may be engaged in a plunger body (22), the elongated body (3) being provided at one end thereof, which end shall stay outside of the syringe body, with
    a pressure element (thumb support); and at the other end, which other end shall stay inside the syringe body, being provided with
    a flexible assembly (4), with claws extending outwardly (5), which engage the plunger body (22), such claws (5) being designed to enhance the radial flexibility of the lower end,
    the plunger body (22) being provided with two parallel surfaces hollowed at a central part thereof by central through-holes (8, 9) of different diameters, the part of the lower surface of the plunger body (22) being provided with the hole (9) of lesser diameter being involved by a flexible membrane (10) and the plunger body (22) being further provided with a cross-shaped cutout (11) disposed centrally, relative to the axis of the through-holes (8, 9), characterized in that:

the upper end (the mouth) of the inner wall of the syringe body has a groove (1) wherein there shall be accommodated a guide washer (21) intended to keep the piston stem/plunger assembly centered in relation to the syringe body; the claws (5) of the flexible assembly (4) shall engage in the cross-shaped cut (11) in the plunger body (22), the claws (5) of the flexible assembly (4) of the piston stem remaining retained in the plunger body (22) by means of the engagement of a supporting pin (6), which pin has a cylindrical body (7) of lesser diameter, in the through holes (8, 9) of the plunger body (22), the supporting pin (6) having a length greater than the thickness of the plunger body (22), the end of its cylindrical body (7) being supported against the internal surface of the flexible membrane (10) that surrounds the lower part of the plunger body (22).

13. A non-reusable syringe, according to claim 12, wherein said flexible claws are formed, at lower ends thereof, with bevels at an angle greater than 45°.

14. A non-reusable syringe, according to claim 12, further comprising an elongated piston stem (3) formed with a compartment (2) at the center of its outer end, said compartment (2) being adapted to accommodate a needle therein.

15. A non-reusable syringe, according to claim 12, further comprising a guide washer (21) formed with a central cutout (12), in the shape of a cross, for guiding the elongated piston stem (3).

16. A non-reusable syringe, according to claim 15, wherein the body of the guide washer (21) is formed with at least one groove (13), thereby rendering said washer frangible.

17. A non-reusable syringe, according to claim 15, wherein the guide washer (21) is welded at a groove (1) of the syringe body, by laser welding (14).

18. A non-reusable syringe, according to claim 12, further comprising an elongated body, named the stem, which has its length reduced longitudinally, to an extent sufficient to create oscillations, in case of any attempted reutilization of the syringe without the guide washer (21).

19. A non-reusable syringe, according to claim 12, further comprising an elongated body, named the stem, which is a separate element from a body (22) of said plunger.

* * * * *